US011813229B2

(12) United States Patent
Vesper et al.

(10) Patent No.: US 11,813,229 B2
(45) Date of Patent: Nov. 14, 2023

(54) TEETH CLEANING COMPOSITION

(71) Applicant: Church & Dwight Co., Inc., Princeton, NJ (US)

(72) Inventors: Caroline Vesper, Baltimore, MD (US); Alysha Moretti, Feasterville, PA (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 17/526,237

(22) Filed: Nov. 15, 2021

(65) Prior Publication Data

US 2022/0151913 A1  May 19, 2022

Related U.S. Application Data

(60) Provisional application No. 63/114,199, filed on Nov. 16, 2020.

(51) Int. Cl.
*A61K 8/9789* (2017.01)
*A61Q 11/00* (2006.01)
*A61K 8/34* (2006.01)

(52) U.S. Cl.
CPC ............ *A61K 8/9789* (2017.08); *A61K 8/345* (2013.01); *A61Q 11/00* (2013.01); *A61K 2800/30* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 4,921,709 | A | 5/1990 | Sole |
| 6,290,933 | B1 | 9/2001 | Durga et al. |
| 6,403,059 | B1 | 6/2002 | Martin et al. |
| 6,419,174 | B1 | 7/2002 | McGill et al. |
| 6,616,916 | B1 | 9/2003 | Karpe et al. |
| 6,740,311 | B2 | 5/2004 | White et al. |
| 6,808,700 | B2 | 10/2004 | Kiji et al. |
| 6,946,119 | B2 | 9/2005 | Gallis et al. |
| 7,033,576 | B2 | 4/2006 | Chevallier et al. |
| 7,255,852 | B2 | 8/2007 | Gallis et al. |
| 7,662,363 | B2 | 2/2010 | Stanier |
| 8,475,847 | B2 | 7/2013 | Ley et al. |
| 8,491,873 | B2 | 7/2013 | Murakami |
| 8,496,977 | B2 | 7/2013 | Medasani |
| 8,609,068 | B2 | 12/2013 | Hagar et al. |
| 8,609,069 | B2 | 12/2013 | Salemme et al. |
| 8,715,625 | B1 | 5/2014 | Rokitowski et al. |
| 8,741,266 | B2 | 6/2014 | Boyd et al. |
| 8,858,921 | B2 | 10/2014 | Schmid et al. |
| 8,906,348 | B2 | 12/2014 | Narasimhan et al. |
| 8,945,517 | B2 | 2/2015 | Hagar et al. |
| 9,114,097 | B1 | 8/2015 | Aminpour |
| 9,220,665 | B2 | 12/2015 | Ashcroft et al. |
| 9,254,253 | B2 | 2/2016 | Plata et al. |
| 9,402,411 | B2 | 8/2016 | Bridges et al. |
| 9,468,592 | B2 | 10/2016 | Plata et al. |
| 9,700,498 | B2 | 7/2017 | Sokolov |
| 9,968,802 | B2 | 5/2018 | Stanier et al. |
| 9,974,723 | B2 | 5/2018 | D'Ambrogio et al. |
| 10,021,899 | B2 | 7/2018 | Markosyan |
| 10,130,567 | B2 | 11/2018 | Deckner et al. |
| 10,172,778 | B2 | 1/2019 | Agerton et al. |
| 10,213,627 | B2 | 2/2019 | Nowak et al. |
| 10,583,314 | B2 | 3/2020 | Bridges et al. |
| 2007/0059256 | A1 | 3/2007 | Kato |
| 2011/0297181 | A1 | 12/2011 | Soloway |
| 2012/0201764 | A1 | 8/2012 | Day et al. |
| 2014/0377188 | A1 | 12/2014 | Strand et al. |
| 2014/0377315 | A1 | 12/2014 | Strand et al. |
| 2015/0164769 | A1 | 6/2015 | Mello et al. |
| 2017/0105911 | A1 | 4/2017 | Budde et al. |
| 2018/0042820 | A1 | 2/2018 | Gadkari et al. |
| 2018/0338892 | A1 | 11/2018 | Budde et al. |
| 2019/0091126 | A1 | 3/2019 | Agerton et al. |
| 2019/0374448 | A1 | 12/2019 | Dolan et al. |
| 2020/0060315 | A1 | 2/2020 | Markosyan |
| 2021/0196621 | A1* | 7/2021 | Modak ................... A61K 31/05 |

FOREIGN PATENT DOCUMENTS

| | | |
|---|---|---|
| CA | 2838826 | 1/2016 |
| CA | 3073776 | 3/2019 |
| CA | 3076692 | 4/2019 |
| CN | 107320408 | 11/2017 |
| EP | 1868689 | 5/2015 |

(Continued)

OTHER PUBLICATIONS

"AE Preserve PX-82", Internet at https://www.aechemie.com/shop/preservatives/natural-preservatives/ae-preserve-px-82/. AE Chemie. Printed Feb. 4, 2022.

"Musa sapientum extract in kids' toothpaste—BBV Kids Organic Toothpaste", Internet search at https://amazejw.com/product/bbv-organic-toothpaste-orange/?lang=en. Printed Jan. 28, 2022.

"Musa sapientum extract in kids' toothpaste. Jack N Jill Natural Toothpaste", Internet search at: https://www.amazon.com/gp/product/B0081ZPVIC/ref=ask_ql_qh_dp_hza. Printed Jan. 28, 2022.

"Native Toothpaste Wild Mint", Internet search at https://www.nativecos.com/products/toothpaste-wild-mint-nf?gclid=EAlalQobChMlj8GcpoLh6wIVwb-tbh3LWgOREAQYAyABEglpVPD_Bwe. Printed Jan. 22, 2022.

"Newco Banana Fluoride Free Kids Toothpaste", Internet search at https://www.newconatural.ca/products/banana-kids-toothpaste. Printed Jan. 28, 2022.

(Continued)

*Primary Examiner* — Nannette Holloman
(74) *Attorney, Agent, or Firm* — Church & Dwight Co., Inc.

(57) ABSTRACT

The present disclosure provides teeth cleaning compositions containing no artificial preservatives and no artificial sweeteners. As such, the teeth cleaning compositions are particularly useful as training toothpaste compositions for children, and particularly very young children. Some aspects of the disclosure relate to teeth cleaning compositions having at least one solvent, at least one thickener, and a banana extract that is effective as a preservative.

18 Claims, No Drawings

(56) References Cited

FOREIGN PATENT DOCUMENTS

| | | |
|---|---|---|
| EP | 2882499 | 8/2016 |
| EP | 1406579 | 11/2016 |
| EP | 2882500 | 8/2017 |
| EP | 2695602 | 2/2018 |
| EP | 2556817 | 1/2019 |
| IN | 202041016847 | 5/2020 |
| JP | 2000136141 | 5/2000 |
| KR | 100947638 | 3/2010 |
| KR | 20160144296 | 12/2016 |
| TW | 201733606 | 10/2017 |
| WO | 2014140054 | 9/2014 |
| WO | 20190885 | 5/2019 |
| WO | 2019120467 | 6/2019 |
| WO | 2019243165 | 12/2019 |
| WO | 2020052855 | 3/2020 |

OTHER PUBLICATIONS

Sekar, "Formulation, Evaluation and Antibacterial Properties of Novel Polyherbal Toothpaste for Oral Care", International Journal of Pharmaceutical and Clinical Research 2016; 8(8): pp. 1155-1158; Aug. 10, 2016. US.

\* cited by examiner

TEETH CLEANING COMPOSITION

CROSS-REFERENCE TO RELATED APPLICATIONS

The present application claims priority to U.S. Provisional Patent Application No. 63/114,199, filed Nov. 16, 2020, the disclosure of which is incorporated herein by reference in its entirety.

FIELD OF THE DISCLOSURE

The present disclosure relates to compositions useful for cleaning and maintaining the aesthetics and health of teeth and promoting oral hygiene. More particularly, the disclosure relates to natural toothpaste compositions that utilize natural preservatives for preventing microbial growth in the composition.

BACKGROUND

This disclosure relates to natural toothpaste/dentifrice compositions that utilize natural preservatives for preventing bacterial/microbial growth in the composition over time and during use.

Typical toothpaste compositions may contain various ingredients, including, for example, fluoride, coloring, flavoring, sweeteners, preservatives, viscosity modifiers, abrasives, and the like. A large variety of oral care products exist on the market today of which almost all are predominately formed from synthetic ingredients that prevent such products from being marketed as "natural" products. Concerns over the health effects of these synthetic ingredients have driven people to seek natural oral care products. In some instances, the use of an entirely natural product may be desirable. However, many natural toothpaste compositions and products suffer from an inability to effectively utilize natural preservatives in those compositions and thus, such products do not effectively prevent bacterial/microbial growth over the entire shelf life of the product.

U.S. Pub. Pat. App. No. 2012/0201764 describes a natural oral care composition with improved taste and texture characteristics. U.S. Pat. No. 9,114,097 describes a natural toothpaste composition which promotes the healthful effects of whitening teeth, refreshing breath, sanitizing the mouth and removing plaque buildup. U.S. Pat. No. 8,715,625 describes natural oral care compositions using naturally processed ingredients that do not require the use of a preservative therein. The compositions described in each of these patent applications do not include a natural preservative component, or even mention the use of natural preservatives.

Accordingly, there is still a desire and a need to provide compositions that provide preservative efficacy through use of natural preservatives and other natural ingredients, such as natural flavorings, sweeteners, and the like.

SUMMARY OF THE DISCLOSURE

In one or more embodiments, the present disclosure provides teeth cleaning compositions that utilize natural preservatives that are effective for preventing microbial growth over time and during use. In one or more embodiments, one or more banana extract(s) can be particularly effective as a natural preservative. As further described herein, banana extract has been found to be effective as a natural preservative in that it is derived directly from a natural product (i.e., bananas) and is effective to prevent bacterial growth over the shelf life of the product. In some embodiments, the present disclosure can provide teeth cleaning compositions that are substantially free of artificial preservatives and/or are substantially free of artificial sweeteners.

One or more aspects of the present disclosure relate to a teeth cleaning composition including at least one solvent, at least one thickener, and a banana extract effective as a preservative. In one or more embodiments, for example, the banana extract may be a modified banana extract. In certain other embodiments, the banana extract may be an enzymatically active banana extract. Generally, the banana extract may be present in an amount of about 1% by weight or greater, based on the total weight of the teeth cleaning composition. In some embodiments, the banana extract may be effective as a preservative such that the teeth cleaning composition exhibits at least 95% efficacy in inhibiting microbial growth when subjected to an Antimicrobial Efficacy Test (AET).

In some embodiments, the at least one solvent may include glycerin and water. For example, in some embodiments, the solvent may include glycerin in an amount of about 10% to about 40% by weight and water in an amount of about 25% to about 75% by weight, based on the total weight of the teeth cleaning composition. In certain other embodiments, the solvent may further include sorbitol in an amount of about 25% to about 45% by weight, based on the total weight of the teeth cleaning composition. In some embodiments, the at least one thickener may include a cellulosic material. For example, in some embodiments, the cellulose material may present in an amount of about 1% to about 4% by weight, based on the total weight of the teeth cleaning composition. In some embodiments, teeth cleaning compositions may also include an abrasive component, e.g., such as hydrated silica. In such embodiments, the hydrated silica may be present in an amount of about 2% to about 12% by weight, based on the total weight of the teeth cleaning composition.

In one or more embodiments, teeth cleaning compositions as described herein may include one or more additional ingredients selected from the group consisting of a natural sweetener, a flavoring agent, a surfactant, and combinations thereof. In some embodiments, the teeth cleaning composition may be substantially free of artificial sweeteners. In some embodiments, the teeth cleaning composition may be substantially free of artificial preservatives. In certain embodiments, the teeth cleaning composition may be in the form of a paste, a gel, or a cream.

In certain embodiments, the present disclosure relates to a teeth cleaning composition comprising: at least one solvent; at least one thickener; and a banana extract effective as a preservative. In further embodiments, the composition can be defined in relation to any one or more of the following statements, which can be combined in any number and order.

The banana extract can be a modified banana extract.

The banana extract can be an enzymatically active banana extract.

The banana extract can be present in an amount of about 1% by weight or greater, based on the total weight of the teeth cleaning composition.

The solvent can comprise glycerin and water.

The solvent can comprise glycerin in an amount of about 10% to about 40% by weight and water in an amount of about 25% to about 75% by weight, based on the total weight of the teeth cleaning composition.

The solvent further can comprise sorbitol in an amount of about 25% to about 45% by weight, based on the total weight of the teeth cleaning composition The thickener can comprise a cellulosic material.

The cellulose material can be present in an amount of about 1% to about 4% by weight, based on the total weight of the teeth cleaning composition.

The teeth cleaning composition further can comprise an abrasive component.

The abrasive can be a hydrated silica.

The hydrated silica can be present in an amount of about 2% to about 12% by weight, based on the total weight of the teeth cleaning composition.

The teeth cleaning composition further can comprise one or more additional ingredients selected from the group consisting of a natural sweetener, a flavoring agent, a surfactant, and combinations thereof.

The teeth cleaning composition can be substantially free of artificial sweeteners.

The teeth cleaning composition can be substantially free of artificial preservatives.

The teeth cleaning composition can be in the form of a paste, a gel, or a cream.

The banana extract can be effective as a preservative such that the teeth cleaning composition exhibits at least 95% efficacy in inhibiting microbial growth when subjected to an Antimicrobial Efficacy Test (AET).

In further embodiments, the present disclosure can relate to a teeth cleaning composition comprising: glycerin in an amount of about 20% to about 40% by weight; water in an amount of about 50% to about 80% by weight; a cellulosic material in an amount of about 2% to about 4% by weight; a banana extract effective as a preservative, the banana extract being present in an amount of at least 0.5% by weight; and a natural sweetener in an amount of at least 0.1% by weight; each of the foregoing amounts being based on the total weight of the teeth cleaning composition.

In still further embodiments, the present disclosure can relate to a teeth cleaning composition comprising: glycerin in an amount of about 10% to about 20% by weight; water in an amount of about 25% to about 45% by weight; sorbitol in an amount of about 25% to about 45% by weight; a cellulosic material in an amount of about 1% to about 3% by weight; hydrated silica in an amount of about 3% to about 12% by weight; a banana extract effective as a preservative, the banana extract being present in an amount of at least 0.5% by weight; and a natural sweetener in an amount of at least 0.1%; each of the foregoing amounts being based on the total weight of the teeth cleaning composition.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present disclosure will become apparent from the following.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The terms "about" and "substantially" used throughout this specification is used to describe and account for relatively small fluctuations. For example, a value of "about" a certain number or value or "substantially" a certain number or value can indicate the specific number or value as well as numbers or values that vary therefrom by ±2% or ±1%. It is understood, however, that the words "about" or substantially" may be expressly excluded or may be replaced by a statement of the specific number or value including any range variation of ±5%, ±4%, ±3%, ±2%, ±1%, ±0.5%, or ±0.1%. All numeric values herein are modified by the term "about" or the term "substantially" whether or not explicitly indicated. The term "substantially" as used herein in relation to a specific condition is similarly understood to encompass the exact condition, as well as minor variations from the specific condition that would be expected to occur due to variations in manufacturing or the like.

In one or more aspects, the present disclosure relates to teeth cleaning compositions that can be particularly useful as training compositions for young children to use while learning good oral hygiene. The present formulations are particularly useful for such purposes in that they can be effective as a toothpaste or other teeth cleaning composition while being formed from materials that can be considered "natural" (i.e., derived from naturally occurring items rather than being synthetically formed). More particularly, the present composition can specifically include a natural preservative that is still effective to prevent microbial growth in the composition. The teeth cleaning composition may be in the form of a paste, a gel, a cream, or similar thickened composition, and the like. For example, a composition substantially in the form of a gel may include at least an aqueous carrier, such as water or other solvent, and a thickener. In some embodiments, the teeth cleaning compositions of the present disclosure may be devoid of artificial sweeteners and/or artificial preservatives. In such embodiments, the teeth cleaning compositions as disclosed herein can be characterized as being substantially free of any artificial sweeteners and/or as being substantially free of any artificial preservatives (e.g., any embodiment as disclosed herein may be completely or substantially free of any artificial sweetener and/or artificial preservative). By "substantially free" it is meant that no artificial sweetener and/or artificial preservative has been intentionally added. For example, certain embodiments can be characterized as having less than 0.01% by weight of artificial sweetener, or less than 0.001%, or even 0% by weight of artificial sweetener. Likewise, certain embodiments can be characterized as having less than 0.01% by weight of artificial preservative, or less than 0.001%, or even 0% by weight of artificial preservative. In particular embodiments, the present compositions may expressly exclude any artificial preservatives and/or may expressly exclude any artificial sweeteners.

In various embodiments of the present disclosure, the teeth cleaning composition can comprise at least a solvent, a thickener, and a natural preservative. A "natural preservative" as described herein, refers to a substance is derived from compounds found in nature (i.e., not man-made/synthetic and which occurs naturally without artificial processing or synthesis with other substances) having preservative characteristics (e.g., the ability to prevent microbial growth thereon). In some embodiments, natural preservatives as described herein may be referred to as being organic. In some embodiments, natural preservatives may be rich in bioactive compounds which may be effective against microorganisms.

In some embodiments, the teeth cleaning composition may include a banana extract that is effective as a preservative. A "banana extract" as described herein, refers to a concentrated plant extract that may particularly be in a substantially liquid form that has been extracted from the plant *Musa sapientum* (banana). Typically, banana extracts are known for their flavoring capabilities in the food, beverage, and consumer goods industry and, thus, are not typically known for providing any preservative and/or antioxidant ability. However, in some embodiments, the banana extracts used herein may be separable from banana extracts that are useful as flavorants and the like and that are not effective as a preservative. For example, the banana extracts useful herein may be modified using various techniques to provide a preservative and/or a disinfectant function by preserving various bioactive compounds in the banana extract, e.g., such as flavonoids, tannins, alkaloids, glycosides, and terpenoids. A "modified" extract as defined herein can refer to a banana extract that has been modified during the formulation process, using solvent extraction techniques (e.g., extracting a liquid extract from a banana peel using an extraction solvent), to increase the activity of the modified banana extract. In such embodiments, the modified banana extract may be used to provide even greater preservative and antioxidant capability than a plain banana extract. In other embodiments, the banana extracts used herein may be modified using various magnetic and/or enzymatic transformation techniques to produce active enzymes within the banana extract. Such "enzymatically active banana extracts" as defined herein, refer to plain banana extracts or modified banana extracts that have been modified during the formulation process, using enzyme-assisted extraction techniques (e.g., pre-treating a banana peel with enzymes prior to solvent extraction), to increase the enzymatic activity of the banana extract. In such embodiments, the enzymatically active banana extract may be used to provide greater preservative and antioxidant capability than a plain or modified banana extract. Example enzymatically active banana extracts are commercially available from AE Chemie, Inc., marketed as AE Preserve™ PX-82. For example, AE Preserve™ PX-82 contains potent enzymes that break/degrade/digest any organic or inorganic substrate from any source and such enzymes may inhibit the growth of various contaminants and microorganisms, including, but not limited to, gram negative bacteria (e.g., such as *Pseudomonas putida, Pseudomonas aeruginosa, Enterobacter cloacae, Escherichia coli*, and the like), certain gram positive bacteria (e.g., such as *Burkholderia cepacia, Staphylococcus aureus*, and the like), certain molds and fungi (e.g., such as *Aspergillus brasiliensis*, and the like), and yeast compounds (e.g., such as *Candida albicans*, and the like). Example extraction techniques using *Musa Sapientum* (banana peels) are described, for example, in "Banana peel (*Musa Sapientum*): A potential natural antioxidant for food preservation," Waghmare, Jyotsna, 15th International Conference on Food Processing & Technology, Institute of Chemical Technology, India, October 27-29, 2016, Rome, Italy.

In some embodiments, a banana extract, including modified banana extracts and enzymatically active banana extracts may be present in the teeth cleaning composition in an amount of about 0.1% to about 5%, about 0.5% to about 3.5%, or about 1% to about 2% by weight, based on the total weight of the composition. In other embodiments, the banana extract may be present in an amount of at least about 0.5%, at least about 1%, at least about 1.5%, or at least about 2% by weight, based on the total weight of the composition. In still other embodiments, the banana extract may be present in an amount of about 2% or less, about 1.5% or less, about 1% or less, or about 0.5% or less (inclusive down to a minimum amount of 0.1% by weight).

It should be noted that the inventors have discovered that use of banana extract, including modified and enzymatically active banana extracts, in the noted amounts can advantageously prevent bacterial/microbial growth in teeth cleaning compositions over the shelf life of the composition. For example, as further described in the appended Examples, compositions according to the present disclosure utilizing a banana extract as a natural preservative have been shown to be 100% effective in inhibiting microbial growth and reducing the amount of microbial contaminants when present in concentrations of 1%, 1.5%, and 2% by weight, based on the total weight of the teeth cleaning composition. Efficacy of the banana extracts were tested using the Antimicrobial Effectiveness Test (AET)—(USP PET Challenge Test USP <51>).

In some embodiments, teeth cleaning compositions as described herein may include a solvent useful for increasing solubilization of one or more further materials used in the teeth cleaning composition. Additionally, one or more solvent can include one or more materials useful for providing flavoring and/or sweetening to the composition in addition to solubilization. In some embodiments, the solvent may include a polyol or, more specifically, a sugar alcohol. However, the teeth cleaning compositions disclosed herein, typically do not include propylene glycol therein and can expressly exclude propylene glycol. Non-limiting examples of suitable solvents include glycerin and sorbitol. In some embodiments, the solvent may include water and/or a combination of water and one or more solvents as discussed herein. In one or more embodiments, a plurality of different solvents may be used. A solvent individually or in a total combined amount can comprise about 5% to about 80% by weight, about 10% to about 40% by weight, about 25% to about 75% by weight, or about 25% to about 55% by weight based on the total weight of the composition. Some solvents may be present in a lower concentration, such as about 5% to about 25%, about 5% to about 20%, or about 5% to about 15% by weight of the total composition. Some solvents may be present in a higher concentration, such as about 30% to about 80%, about 30% to about 50%, or about 30% to about 40% by weight of the total composition. More particularly, glycerin may be present in an amount of about 10% to about 40% by weight, and/or water may be present in an amount of about 25% to about 75% by weight, and/or sorbitol can be present in an amount of about 25% to about 45% by weight.

In some embodiments, teeth cleaning compositions as described herein may include a thickener. The thickener can be any material suitable for achieving a suitable consistency such that the composition exhibits a self-sustaining volume and is not rapidly disintegrated in the mouth of a user of the teeth cleaning composition. In some embodiments, for example, it can be useful to provide the composition substantially in the form of a gel or a paste. In other embodiments, for example, it can be useful to provide the composition substantially in the form of a cream. Suitable thickeners can be chosen to be used alone or in combination to achieve the desired consistency. For example, in some embodiments, suitable thickeners can include gelling agents, such as gelatin and pectin; however, it can be desirable to utilize thickeners that provide thickening without solidification. In some embodiments, cellulosic materials in particular can be used as the thickener. For example, carboxymethylcellulose and/or cellulose gums in particular can be useful. Other gums, such as xanthan gum, likewise may be used. In one or more embodiments, a plurality of different thickeners may be used. In some embodiments, a silica material may be used as the thickener or in combination with one or more other thickeners. For example, hydrated silica may be used as a thickener. In embodiments wherein hydrated silica is used as the thickener, or in combination with another thickener, sorbitol can be included as a solvent in such compositions to help with dissolution of the hydrated silica. Advantageously, silica-based thickeners (e.g., such as hydrated silica) may be less likely to result in changes to rheology over the shelf-life of the composition as compared to cellulosic gums. A thickener individually or in a total combined amount can comprise about 0.1% to about 15%, about 0.5% to about 14%, about 1% to about 12%, about 2% to about 12%, or about 1.5% to about 4% by weight, based on the total weight of the composition. For example, a cellulosic material may be present specifically in an amount of about 1% to about 4% by weight. A hydrated silica may be present in an amount of about 2% to about 12% by weight.

In various embodiments, the teeth cleaning composition can further comprise one or more additional ingredients. For example, the teeth cleaning composition can comprise at least one of a natural sweetener, a flavoring agent, a soothing agent, a cooling agent, one or more viscosity modifiers, a surfactant, an abrasive, and/or other additives. In some embodiments, one or more materials may provide a plurality of functions. For example, thickeners such has hydrated silica may be useful as both a thickener and an abrasive. Any of the one or more additional ingredients individually may be present in an amount of about 0.01% to about 1%, about 0.02% to about 0.5%, or about 0.03% to about 0.2% by weight, based on the total weight of the teeth cleaning composition.

In some embodiments, the teeth cleaning composition may comprise a sweetener. In particular, the sweetener may be in the form of a natural sweetener. For example, as noted above, the teeth cleaning composition may be free of artificial sweeteners in some embodiments. In some embodiments, the sweetener may include any natural sweetener, e.g., such as *Stevia rebaudiana* leaf extract, xylitol, erythritol, monkfruit (e.g., such as an extract from a plant of the species, *Siratitia grosvenorii* (known as "Monkfruit extract"), and the like. In some embodiments, a sweetener can be present in an amount in the range of about 0.01 to about 5 weight percent, about 0.05 to about 2 weight percent, about 0.1 to about 1 weight percent, or about 0.2 to about 0.5 weight percent, based on the total weight of the teeth cleaning composition. In various embodiments, a sweetener can be present in an amount of at least about 0.01 weight percent, at least about 0.1 weight percent, or at least about 0.5 weight percent, based on the total weight of the teeth cleaning composition (e.g., with a maximum concentration of about 10 weight percent).

In some embodiments, the teeth cleaning composition may comprise a flavoring agent or a combination of flavoring agents. The flavoring agents can be configured to provide sweetness and/or another desired flavor to the composition. In particular, the flavoring agent may be a natural flavor that does not provide any artificial flavoring. For example, suitable flavoring agents may provide fruit flavors (e.g., strawberry, cherry, banana, apple, pear) to the composition. Similarly, one or more natural fruit flavors may be used. In some embodiments, one or more flavoring agents can be present in an amount in the range of about 0.01 to about 10 weight percent, about 0.05 to about 5 weight percent, about 0.1 to about 2 weight percent, or about 0.5 to about 1 weight percent, based on the total weight of the teeth cleaning composition. The flavoring agent(s) can be present in an amount of at least about 0.01 weight percent, at least about 0.5 weight percent, at least about 1 weight percent, or at least about 2 weight percent, based on the total weigh of the teeth cleaning composition (e.g., with a maximum concentration of about 10 weight percent).

In some embodiments, the teeth cleaning composition may optionally include one or more surfactants. A surfactant can be any material useful for stabilizing a mixture and improving solubilization of the various ingredients otherwise discussed herein. In some embodiments, surfactants can be particularly useful as a rheology modifier to reduce flowability of the composition without significantly increasing the viscosity of the composition and thus improve contact time of the composition in the mouth. In some embodiments, the surfactant may be in the form of a natural surfactant, e.g., such surfactant may include, but are not limited to, cocamidopropyl betaine, amino acid based surfactants (e.g., such as sodium cocoyl glutamate, sodium lauryl sarcosinate, sodium methyl cocoyl taurate, sodium lauryl sulfate, and the like), and glucoside surfactants (e.g., such as decyl glucoside, cocoyl glucoside, lauryl glucoside, and the like). In one or more embodiments, a plurality of different surfactants may be used. A surfactant individually or in a total combined amount can comprise about 0.1% to about 5%, about 0.25% to about 4%, about 0.5% to about 3.5%, or about 1% to about 3% by weight, based on the total weight of the teeth cleaning composition.

In some embodiments, the teeth cleaning composition may optionally include one or more abrasive components. An abrasive may provide some level of abrasion against the surface of a user's teeth and/or may provide some level of additional cleaning benefits due to such abrasive qualities. In some embodiments, a silica material may be used as an abrasive component. For example, hydrated silica may be used in teeth cleaning compositions as described herein. An abrasive individually or in a total combined amount can comprise about 0.1% to about 12%, about 1% to about 10%, about 2% to about 8%, about 3% to about 7%, or about 4% to about 6% by weight, based on the total weight of the teeth cleaning composition.

EXAMPLES

Example 1

Two embodiments of a teeth cleaning composition (referred to as "Formulation 1" and "Formulation 2") according to the present disclosure are provided. Table 1 below provides ingredients included in an embodiment of the teeth cleaning composition of the present disclosure. Table 1 also includes the weight percentage of each ingredient, based on the total weight of the teeth cleaning composition. It is noted that Formulation 1 is in the form of a toothpaste gel and contains no artificial sweeteners, preservatives, or flavorings therein.

TABLE 1

Formulation 1

| Ingredient | Function | Concentration (wt. %) |
|---|---|---|
| Glycerin | Solvent | 10-20% |
| Water | Solvent | 25-45% |
| Sorbitol | Solvent | 25-45% |
| Cellulose Gum | Thickener | 1-3% |
| Hydrated Silica | Thickener | 2-8% |
| Hydrated Silica | Abrasive | 2-8% |
| Stevia Rebaudiana Leaf Extract | Sweetener | 0.1-2% |
| Cocamidopropyl Betaine | Surfactant | 0.1-2% |
| Musa Sapientum (Banana) Extract | Preservative | 0.1-2% |
| Flavor | Flavoring Agent | 0.1-2% |

Table 2 below provides ingredients included in an embodiment of the teeth cleaning composition of the present disclosure. Table 2 also includes the weight percentage of each ingredient, based on the total weight of the teeth cleaning composition. It is noted that Formulation 2 is in the form of a toothpaste gel and contains no artificial sweeteners, artificial preservatives, or artificial flavorings therein.

TABLE 2

Formulation 2

| Ingredient | Function | Concentration (wt. %) |
|---|---|---|
| Glycerin | Solvent | 20-40% |
| Water | Solvent | 50-80% |
| Cellulose Gum | Thickener | 2-4% |
| Stevia Rebaudiana Leaf Extract | Sweetener | 0.1-2% |
| Cocamidopropyl Betaine | Surfactant | 0.1-2% |
| Musa Sapientum (Banana) Extract | Preservative | 0.1-2% |
| Flavor | Flavoring Agent | 0.1-2% |

Example 2

Testing was conducted on a sample formulation of a teeth cleaning composition containing banana extract in an amount of 2% by weight, based on the total weight of the teeth cleaning composition (referred to as "Sample A"), to determine the antimicrobial effectiveness of banana extract as a preservative. Efficacy of the compositions containing banana extracts were evaluated using the Antimicrobial Effectiveness Test (AET)—(USP PET Challenge Test USP <51>). During testing, six inoculum cultures of the following microorganisms: (1) Escherichia coli (E. coli), (2) Staphylococcus aureus (S. aereus), (3) Pseudomonas aeruginosa (P. aeruginosa), (4) Candida albicans (C. albicans), (5) Aspergillus brasiliensis (A. brasiliensis) or Aspergillus niger (A. niger), and (6) Burkholderia cepacia (B. cepacia), were added to the sample medium and allowed to incubate in six inoculated containers for a period of about 12 hours to about 4 weeks at a temperature of about 30° C. to about 40° C. In addition to the six inoculum cultures, a seventh control sample was added to the sample medium and allowed to incubate under similar conditions. The microbial concentration of the inoculum culture was observed during the duration of testing and measurements were taken upon initiation of the test, after 1 week, after 2 weeks, after 3 weeks, and after 4 weeks. Three separate AET tests were performed on Sample A and the representative data for those tests is demonstrated in Tables 3, 4, and 5 shown below.

TABLE 3

| Organism | Initial Concentration (inoculum/g) | Concentration after 1 week (inoc/g) | Concentration after 2 weeks (inoc/g) | Concentration after 3 weeks (inoc/g) | Concentration after 4 weeks (inoc/g) |
|---|---|---|---|---|---|
| E. coli | $5.2 \times 10^5$ | <10 | <10 | <10 | <10 |
| S. aureus | $3.9 \times 10^5$ | <10 | <10 | <10 | <10 |
| P. aeruginosa | $4.7 \times 10^5$ | <10 | <10 | <10 | <10 |
| C. albicans | $4.5 \times 10^5$ | <10 | <10 | <10 | <10 |
| A. brasiliensis | $3.2 \times 10^5$ | 30 | <10 | <10 | <10 |
| B. cepacia | $7.1 \times 10^5$ | <10 | <10 | <10 | <10 |
| Negative Control | N/A | <10 | <10 | <10 | <10 |

As shown in Table 3, the concentration of each of the microorganisms showed an exponential reduction after 1 week and maintained that reduction in concentration after 2, 3, and 4 weeks (e.g., exhibiting a microbial concentration of less than 10 inoc/g). Such results demonstrate the efficacy of the banana extract as a preservative in the tested sample, as the test results indicate that the banana extract was approximately 100% effective in preventing microbial growth in the sample composition over the observed time period when compared to the negative control sample. These results are consistent with the requirements for antimicrobial effectiveness as outlined using the USP <51> Antimicrobial Effectiveness Test using the criteria for "Category 3—Oral products other than antacids" (i.e., bacteria samples must meet the minimum criteria of not less than 1.0 log reduction from the initial count at 14 days and no increase from the 14 days' count at 28 days; yeast and mold samples must meet the minimum criteria of no increase from the initial calculated count at 14 and 28 days).

TABLE 4

| Organism | Initial Concentration (inoculum/g) | Concentration after 1 week (inoc/g) | Concentration after 2 weeks (inoc/g) | Concentration after 3 weeks (inoc/g) | Concentration after 4 weeks (inoc/g) |
|---|---|---|---|---|---|
| E. coli | $6.6 \times 10^5$ | <10 | <10 | <10 | <10 |
| S. aureus | $3.7 \times 10^5$ | <10 | <10 | <10 | <10 |
| P. aeruginosa | $7.9 \times 10^5$ | <10 | <10 | <10 | <10 |
| C. albicans | $4.4 \times 10^5$ | <10 | <10 | <10 | <10 |
| A. niger | $3.2 \times 10^5$ | <10 | <10 | <10 | <10 |
| B. cepacia | $4.5 \times 10^5$ | <10 | <10 | <10 | <10 |
| Negative Control | N/A | <10 | <10 | <10 | <10 |

As shown in Table 4, the concentration of each of the microorganisms showed an exponential reduction after 1 week and maintained that reduction in concentration after 2, 3, and 4 weeks (e.g., exhibiting a microbial concentration of less than 10 inoc/g). Such results demonstrate the efficacy of the banana extract as a preservative in the tested sample, as the test results indicate that the banana extract was approximately 100% effective in preventing microbial growth in the sample composition over the observed time period when compared to the negative control sample. These results are consistent with the requirements for antimicrobial effectiveness as outlined using the USP <51> Antimicrobial Effectiveness Test using the criteria for "Category 3—Oral products other than antacids" (i.e., bacteria samples must meet the minimum criteria of not less than 1.0 log reduction from the initial count at 14 days and no increase from the 14 days' count at 28 days; yeast and mold samples must meet the minimum criteria of no increase from the initial calculated count at 14 and 28 days).

TABLE 5

| Organism | Initial Concentration (inoculum/g) | Concentration after 1 week (inoc/g) | Concentration after 2 weeks (inoc/g) | Concentration after 3 weeks (inoc/g) | Concentration after 4 weeks (inoc/g) |
|---|---|---|---|---|---|
| E. coli | $4.9 \times 10^5$ | <10 | <10 | <10 | <10 |
| S. aureus | $5.5 \times 10^5$ | <10 | <10 | <10 | <10 |
| P. aeruginosa | $6.7 \times 10^5$ | <10 | <10 | <10 | <10 |
| C. albicans | $5.8 \times 10^5$ | <10 | <10 | <10 | <10 |
| A. brasiliensis | $4.1 \times 10^5$ | 160 | <10 | <10 | <10 |
| B. cepacia | $7.4 \times 10^5$ | <10 | <10 | <10 | <10 |
| Negative Control | N/A | <10 | <10 | <10 | <10 |

As shown in Table 5, the concentration of each of the microorganisms showed an exponential reduction after 1 week and maintained or improved that reduction in concentration after 2, 3, and 4 weeks (e.g., exhibiting a microbial concentration of less than 10 inoc/g). Such results demonstrate the efficacy of the banana extract as a preservative in the tested sample, as the test results indicate that the banana extract was approximately 100% effective in preventing microbial growth in the sample composition over the observed time period when compared to the negative control sample. These results are consistent with the requirements for antimicrobial effectiveness as outlined using the USP <51> Antimicrobial Effectiveness Test using the criteria for "Category 3—Oral products other than antacids" (i.e., bacteria samples must meet the minimum criteria of not less than 1.0 log reduction from the initial count at 14 days and no increase from the 14 days' count at 28 days; yeast and mold samples must meet the minimum criteria of no increase from the initial calculated count at 14 and 28 days).

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A teeth cleaning composition comprising:
    at least one solvent;
    at least one thickener; and
    a banana extract effective as a preservative such that the teeth cleaning composition exhibits at least 95% efficacy in inhibiting microbial growth when subjected to an Antimicrobial Efficacy Test (AET).

2. The teeth cleaning composition of claim 1, wherein the banana extract is a modified banana extract.

3. The teeth cleaning composition of claim 1, wherein the banana extract is an enzymatically active banana extract.

4. The teeth cleaning composition of claim 1, wherein the banana extract is present in an amount of about 1% by weight or greater, based on the total weight of the teeth cleaning composition.

5. The teeth cleaning composition of claim 1, wherein the solvent comprises glycerin and water.

6. The teeth cleaning composition of claim 5, wherein the solvent comprises glycerin in an amount of about 10% to about 40% by weight and water in an amount of about 25% to about 75% by weight, based on the total weight of the teeth cleaning composition.

7. The teeth cleaning composition of claim 6, wherein the solvent further comprises sorbitol in an amount of about 25% to about 45% by weight, based on the total weight of the teeth cleaning composition.

8. The teeth cleaning composition of claim 1, wherein the thickener comprises a cellulosic material.

9. The teeth cleaning composition of claim 8, wherein the cellulose material is present in an amount of about 1% to about 4% by weight, based on the total weight of the teeth cleaning composition.

10. The teeth cleaning composition of claim 1, wherein the teeth cleaning composition further comprises an abrasive component.

11. The teeth cleaning composition of claim 10, wherein the abrasive is a hydrated silica.

12. The teeth cleaning composition of claim 11, wherein the hydrated silica is present in an amount of about 2% to about 12% by weight, based on the total weight of the teeth cleaning composition.

13. The teeth cleaning composition of claim 1, further comprising one or more additional ingredients selected from the group consisting of a natural sweetener, a flavoring agent, a surfactant, and combinations thereof.

14. The teeth cleaning composition of claim 1, wherein the teeth cleaning composition is substantially free of artificial sweeteners.

15. The teeth cleaning composition of claim 1, wherein the teeth cleaning composition is substantially free of artificial preservatives.

16. The teeth cleaning composition of claim 1, wherein the teeth cleaning composition is in the form of a paste, a gel, or a cream.

17. A teeth cleaning composition comprising:
glycerin in an amount of about 20% to about 40% by weight;
water in an amount of about 50% to about 80% by weight;
a cellulosic material in an amount of about 2% to about 4% by weight;
a banana extract effective as a preservative, the banana extract being present in an amount of at least 0.5% by weight; and
a natural sweetener in an amount of at least 0.1% by weight;
each of the foregoing amounts being based on the total weight of the teeth cleaning composition.

18. A teeth cleaning composition comprising:
glycerin in an amount of about 10% to about 20% by weight;
water in an amount of about 25% to about 45% by weight;
sorbitol in an amount of about 25% to about 45% by weight;
a cellulosic material in an amount of about 1% to about 3% by weight;
hydrated silica in an amount of about 3% to about 12% by weight;
a banana extract effective as a preservative, the banana extract being present in an amount of at least 0.5% by weight; and
a natural sweetener in an amount of at least 0.1%;
each of the foregoing amounts being based on the total weight of the teeth cleaning composition.

* * * * *